United States Patent
Fukushima

(10) Patent No.: US 9,603,880 B2
(45) Date of Patent: Mar. 28, 2017

(54) **COMPOSITION CONTAINING BACTERIUM BELONGING TO GENUS *LACTOBACILLUS***

(71) Applicant: SUNTORY HOLDINGS LIMITED, Osaka-shi, Osaka (JP)

(72) Inventor: Eiji Fukushima, Kawasaki (JP)

(73) Assignee: SUNTORY HOLDINGS LIMITED, Tokyo (JP)

( * ) Notice: Subject to any disclaimer, the term of this patent is extended or adjusted under 35 U.S.C. 154(b) by 0 days.

(21) Appl. No.: 14/784,064

(22) PCT Filed: Apr. 16, 2014

(86) PCT No.: PCT/JP2014/060812
§ 371 (c)(1),
(2) Date: Oct. 13, 2015

(87) PCT Pub. No.: WO2014/171478
PCT Pub. Date: Oct. 23, 2014

(65) Prior Publication Data
US 2016/0058807 A1    Mar. 3, 2016

(30) Foreign Application Priority Data
Apr. 17, 2013   (JP) ................ 2013-086576

(51) Int. Cl.
| | | |
|---|---|---|
| *A01N 63/00* | (2006.01) | |
| *A61K 35/747* | (2015.01) | |
| *C12R 1/225* | (2006.01) | |
| *A23L 33/135* | (2016.01) | |
| *A61K 35/00* | (2006.01) | |

(52) U.S. Cl.
CPC .......... *A61K 35/747* (2013.01); *A23L 33/135* (2016.08); *C12R 1/225* (2013.01); *A61K 2035/115* (2013.01)

(58) Field of Classification Search
None
See application file for complete search history.

(56) References Cited

U.S. PATENT DOCUMENTS

| | | | |
|---|---|---|---|
| 5,879,729 A | 3/1999 | King Solis et al. | |
| 8,603,461 B2 * | 12/2013 | Stanton ................. | A23K 1/009 424/93.45 |
| 2004/0071680 A1 | 4/2004 | Song et al. | |
| 2004/0115179 A1 | 6/2004 | Liu et al. | |
| 2005/0112112 A1 | 5/2005 | Park et al. | |
| 2010/0216212 A1 | 8/2010 | Morita et al. | |
| 2011/0311501 A1 | 12/2011 | Morita et al. | |
| 2012/0027736 A1 | 2/2012 | Morita et al. | |

FOREIGN PATENT DOCUMENTS

| | | |
|---|---|---|
| EP | 663153 A1 | 7/1995 |
| JP | 7-250649 A | 10/1995 |
| JP | 2004/73178 A | 3/2004 |
| JP | 2004-154131 A | 6/2004 |
| JP | 2007-135596 A | 6/2007 |
| JP | 2007-284360 A | 11/2007 |
| JP | 2008-179595 A | 8/2008 |
| JP | 2011172506 A | 9/2011 |
| JP | 2011206057 A | 10/2011 |
| JP | 2011-217715 A | 11/2011 |
| WO | 2004/014403 A1 | 2/2004 |
| WO | 2007/043933 A1 | 4/2007 |
| WO | 2010/136891 A1 | 12/2010 |

OTHER PUBLICATIONS

Zhou et al. Biosci Biotechnol Biochem. Mar. 7, 2013, 77(3):591-594.*
Zavisic et al. "Probiotic features of two oral lactobacillus isolates". Brazilian Journal of Microbiology. 2012, pp. 418-428. )*
Shu Yoei et al. Japan Society for Bioscience, Biotechnology, and Agrochemistry Taikai Koen Yoshishu, 2011, vol. 2011, p. 67.*
Maekawa et al. Japan Society for Bioscience, Biotechnology, and Agrochemistry Taikai Koen Yoshishu, 2011, vol. 2011, p. 67.*
International Search Report dated Jun. 3, 2014, issued in counterpart Application No. PCT/2014/060812 (2 pages).
International Search Report dated Jun. 3, 2014, issued in counterpart Application No. PCT/JP2014/060811 (2 pages).
Maekawa, Toshihiro et al. "Lactobacillus pentosus S-PT84-kabu ni yoru kohiman koka", Japan Society for Bioscience, Biotechnology, and Agrochemistry Taikai Koen Yoshishu, 2011, vol. 2011, p. 67.
M., Sogawa et al., "Awa (Tokushima) lactate-fermented tea as well as green tea enhance the effect of diet restriction on obesity in rats", J. Med. Invest., 2009, vol. 56, pp. 42-48.
Shu, Yuei et al., "Rat ni Okeru Nyusankin no Shokugo Ko Triacylglycerol Kessho Kaizen Sayo", Japan Society for Bioscience, Biotechnology, and Agrochemistry Taikai Koen Yoshishu, 2011, vol. 2011, p. 67.
Kaminogawa, Shuichi, "Physiological Function of Lacttic Acid bacteria for Human Health," Aug. 31, 2007, CMC Publishing Co., Ltd., pp. 160-162.

(Continued)

*Primary Examiner* — Vera Afremova

(74) *Attorney, Agent, or Firm* — Westerman, Hattori, Daniels & Adrian, LLP

(57) ABSTRACT

A composition containing a *Lactobacillus pentosus* TUA4337L strain (accession number: NITE BP-1479), characterized in that the strain has proliferation ability in the small intestines and/or the large intestine, and preferably the small intestines, after having survived in the intestinal tract. Since the composition of the present invention contains lactic acid bacteria having proliferation ability in the intestinal tract, when ingested in the body, the lactic acid bacteria survive to the intestinal tract and proliferate, whereby the fat absorption can be blocked, and the weight gains can be blocked, so that the composition can be suitably used for the purposes of dieting effects.

3 Claims, 2 Drawing Sheets

(56) References Cited

OTHER PUBLICATIONS

Ishida, Yuu et al., "Isolation and characterization of a Lactobacillus acidophilus strain L92 that can survive in human gastrointestinal tract", Japanese Journal of Lactic Acid Bacteria, 2001, vol. 12, pp. 28-35.
Takahashi, Hidetoshi et al , "Monitoring and Survival of Lactobacillus gasseri SBT2055 in the Human Intestinal Tract", Aug. 3 2006, Technology and Research Institute, Snow Brand Milk Products Co., Ltd., pp. 867-870.
Rochet, Violaine. "Survival of Bifidobacterium animalis DN-173 010 in the Faecal Microbiota after Administration in Lyophilised Form or in Fermented Product—A Randomised Study in Healthy Adults", Journal of Molecular Microbiology and Biotechnology, 2007, S. Karger AG. Basel, 128-136.
Extended European Search Report dated Nov. 2, 2016 from EP 14 78 5100.

\* cited by examiner

US 9,603,880 B2

COMPOSITION CONTAINING BACTERIUM BELONGING TO GENUS *LACTOBACILLUS*

TECHNICAL FIELD

The present invention relates to a composition containing a bacterium belonging to the genus *Lactobacillus*. More specifically, the present invention relates to a composition containing novel *Lactobacillus pentosus*.

BACKGROUND ART

Some of lactic acid bacteria and Bifidobacteria have excellent physiological activities such as an intestine regulating activity and immunostimulating activity, and have been used in various applications depending upon the properties of the bacterial species. Among them, recently, studies on dieting effects by taking these bacteria have been progressed, and many reports have been made.

For example, Patent Publication 1 reports that *Lactobacillus rhamnosus* ATCC53103 strain degrades a lipid (triacyl glycerol) which is causative of obesity, thereby blocking its absorption into the body. In addition, it has been known that *L. brevis* KB290, which is one kind of vegetable lactic acid bacteria, reaches to the intestines in a live state, thereby showing excellent intestinal viable rates and intestinal tract survivability (however, the number of bacteria excreted is smaller than the number of ingested bacteria) (see Non-Patent Publication 1). Also, the following Non-Patent Publication 2 has reported that *Lactobacillus acidophilus* L-92 strain is collected from feces in an amount 93% of the number of ingested bacteria, so that the strain has excellent intestinal tract survivability, and the following Non-Patent Publication 3 has reported that the survivability of *L. gasseri* SBT2055 in the intestinal tract is examined, and 100 g of a fermented milk containing $1 \times 10^6$ to $5 \times 10^6$ cfu/g of the bacteria is administered, and as a result, the bacteria are detected from feces maximally at $1 \times 10^5$ cfu/g or so.

On the other hand, as to the Bifidobacteria, it has been reported that *Bifidobacterium animalis* subspecies *lactis* GCL2505 strain not only has intestinal tract survivability in which the strain reaches to the intestines in a live state after the oral ingestion but also shows remarkable proliferation ability within the intestinal tract (see, Patent Publication 2). The following Non-Patent Publication 4 has reported that when *B. animalis* ssp. *lactis* DN-173 010 is administered to adults, 20% or so of the DN-173 010 is detected from stools, relative to the number of bacteria ingested.

RELATED ART REFERENCES

Patent Publications

Patent Publication 1: Japanese Patent Laid-Open No. 2011-206057
Patent Publication 2: Japanese Patent Laid-Open No. 2011-172506

Non-Patent Publications

Non-Patent Publication 1: "Physiological Function of Lactic Acid Bacteria for Human Health," Aug. 31, 2007, CMC Publishing CO., LTD., 160-162
Non-Patent Publication 2: *Japanese Journal of Lactic Acid Bacteria*, 2001, 12, "Isolation and characterization of a *Lactobacillus acidophilus* strain L92 that can survive in in human gastrointestinal tract," 28-35
Non-Patent Publication 3: *Microbiol. Immunol.*, 2006, 50, "Monitoring and survival of *Lactobacillus gasseri* SBT2055 in the human intestinal tract," 867-870
Non-Patent Publication 4: *J. Mol. Microbiol. Biotechnol.*, 2008, 14, "Survival of *Bifidobacterium animalis* DN-173 010 in the faecal microbiota after administration in lyophilized form or in fermented product—a randomized study in healthy adults," 128-136

SUMMARY OF THE INVENTION

Problems to be Solved by the Invention

However, since fat absorption mainly takes place in the small intestines, even if *Bifidobacterium* which is usually proliferated in the large intestine shows proliferation ability in the intestinal tract, the blocking of fat absorption is not sufficient. Further, the lactic acid bacteria are known to act upstream the large intestine, but reports on the bacterial species showing proliferation ability in the intestinal tract have not yet been made.

An object of the present invention is to provide a composition containing lactic acid bacteria showing proliferation ability in the intestinal tract.

Means to Solve the Problems

The present invention relates to a composition containing a *Lactobacillus pentosus* TUA4337L strain (accession number: NITE BP-1479), characterized in that the strain has proliferation ability in the intestinal tract.

Effects of the Invention

When the composition of the present invention is ingested, since the lactic acid bacteria having proliferation ability in the intestinal tract proliferate, some excellent effects that physiological activity of the bacterial cells is enhanced are exhibited, which in turn result in obtaining dieting effects.

MODES FOR CARRYING OUT THE INVENTION

Figure 1:
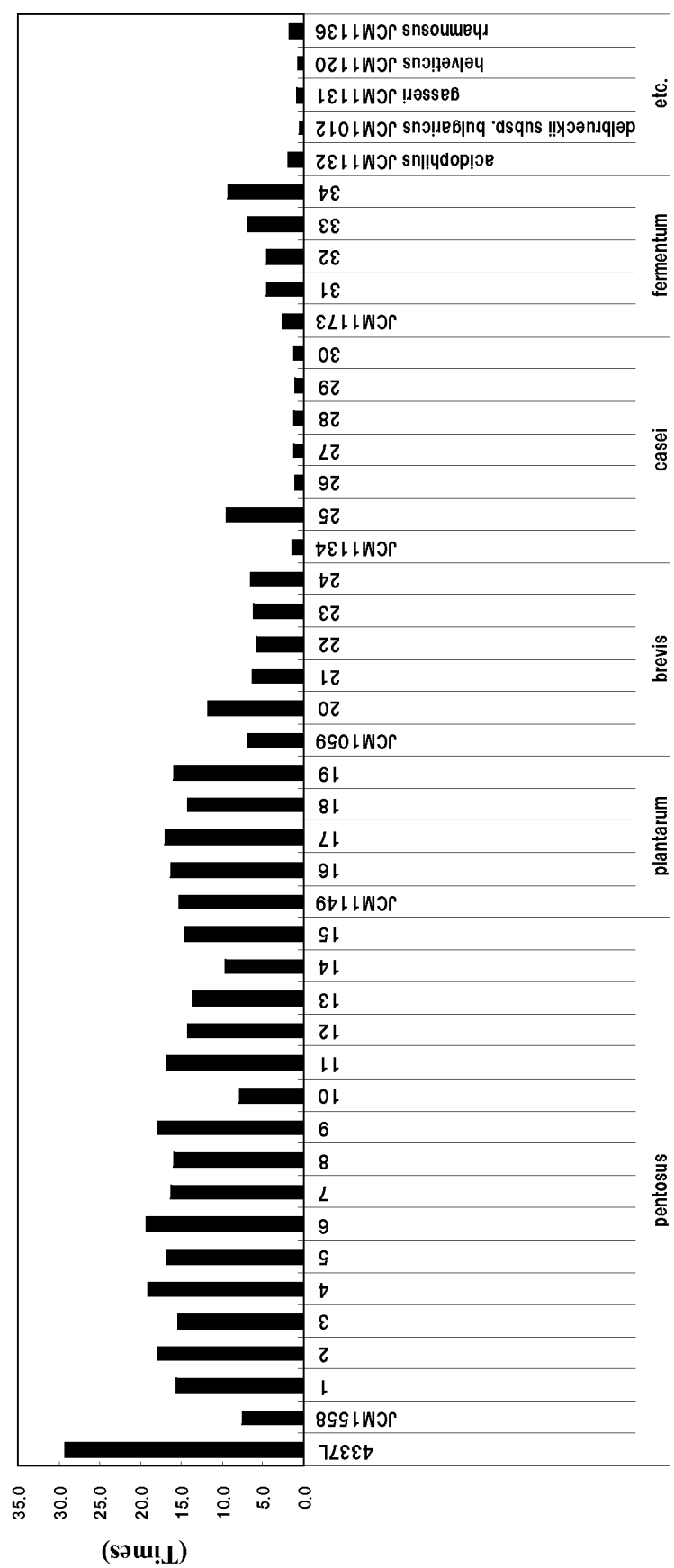
FIG. 1 is a graph showing the results of screening in artificial intestinal solutions.

The composition of the present invention has a large feature that the composition contains lactic acid bacteria of a *Lactobacillus pentosus* TUA4337L strain (hereinafter also referred to as the lactic acid bacteria of the present invention), wherein the strain has proliferation ability in the intestinal tract.

The lactic acid bacteria of the present invention are a *Lactobacillus pentosus* TUA4337L strain, characterized in that the strain has proliferation ability in the intestinal tract. Here, the phrase "has proliferation ability in the intestinal tract" or "proliferating in the intestinal tract" as used herein means that the strain after having survived in the intestinal tract proliferates in the small intestines and/or the large intestine, and preferably the small intestines, and the degree of proliferation ability can be evaluated as "being proliferative" in a case where the numerical value is ten times or more of the $OD_{660}$ at inoculation when the strain is cultured in an artificial intestinal solution at 37° C. for 6 hours.

The present inventors have examined proliferation ability of about 480 kinds of lactic acid bacteria owned by the present inventors in artificial intestinal solutions, and have administered suspensions of the bacteria belonging to *Lactobacillus pentosus* selected therefrom to animals. As a result, the present inventors have found out that the *Lactobacillus pentosus* TUA4337L strain is significantly larger in the number of bacteria excreted than the number of bacteria administered. The present invention has been perfected thereby.

The *Lactobacillus pentosus* TUA4337L strain is deposited at Patent Microorganisms Depositary, National Institute of Technology and Evaluation, Incorporated Administrative Agency (2-5-8 Kazusakamatari, Kisarazu-shi, Chiba-ken, Japan) with the identification reference of NRIC 0883, under the accession number of NITE BP-1479 dated with an international deposition date of Dec. 10, 2012. The *Lactobacillus pentosus* TUA4337L strain is hereinafter simply referred to as TUA4337L strain.

The bacteriological characteristics of the TUA4337L strain are shown in Tables 1 and 2. The sugar assimilation activity of Table 2 is the results of measurement using a bacteria identification kit API 50CH (BIOMETRIEUX). Here, "+" means an assimilated sugar, and "−" means an unassimilated sugar in Table 2.

As described in detail in Examples set forth below, the TUA4337L strain has the characteristics of increasing the number of bacteria excreted as compared to the number of bacteria ingested, in other words, having proliferation ability in the intestinal tract. In addition, as the proliferation ability in the intestinal tract, the number of bacteria after 6-hour culture in an artificial intestinal solution at 37° C. is preferably 10 times or more, more preferably 15 times or more, even more preferably 20 times or more, and still even more preferably 25 times or more, of the number of bacteria at the beginning of culture of the bacteria used as a standard.

In addition, the sequence of recA gene (SEQ ID NO: 1) decoded from DNA extracted from the TUA4337L strain has 99% homology to the sequence of recA gene of *Lactobacillus pentosus* IG1 strain. Here, the homology as used herein is shown as a degree of similarity by scores using, for example, a search program BLAST using the algorithm developed by Altschul et al. (*The Journal of Molecular Biology*, 215, 403-410 (1990)).

The medium for culturing the TUA4337L strain is not particularly limited, and the medium includes media containing ordinary carbon sources, nitrogen sources, inorganic salts, organic nutrients, and the like. In addition, the culture with an agar medium or a liquid medium can be performed. The culture temperature is preferably from 10° to 45° C., more preferably from 15° to 42° C., even more preferably from 28° to 38° C., and even more preferably from 35° to 37° C., and a proliferative pH is preferably a pH of from 3.0 to 12.5, and more preferably a pH of from 3.5 to 12.0.

The composition of the present invention contains a *Lactobacillus pentosus* TUA4337L strain having proliferation ability in the intestinal tract mentioned above in various forms.

The forms of the *Lactobacillus pentosus* TUA4337L strain contained in the composition of the present invention include lactic acid bacteria themselves, including viable bacteria and dead bacteria, lactic acid bacteria inclusions and processed cells of lactic acid bacteria, and the like. The viable bacteria can be obtained from lactic acid bacteria inclusions such as a culture medium containing lactic acid bacteria. The dead bacteria can be obtained, for example, by subjecting viable bacteria to heating, ultraviolet irradiation, formalin treatment, an acid treatment or the like. The resulting viable bacteria or dead bacteria can be further produced into processed cells by subjecting the bacteria to grinding, crushing, or the like. Here, the lactic acid bacteria in each of the above forms are preferably viable bacteria from the viewpoint of fully exhibiting the effects of proliferating in the intestinal tract, and dead bacteria may be admixed therewith.

The above lactic acid bacteria include, for example, viable bacteria, wet bacteria, dry bacteria, and the like. The above lactic acid bacteria inclusions include, for example, suspensions of lactic acid bacteria, cultured cells of lactic acid bacteria (including bacterial cells, supernatant, and medium ingredients), and cultured media containing lactic acid bacteria (obtained by removing solid contents from the cultured cells of bacteria). In addition, the above processed cells of lactic acid bacteria include, for example, ground cells, crushed cells, liquefied cells (extracts etc.), concentrates, paste-like cells, dried cells (spray-dried cells, freeze-dried cells, vacuum-dried cells, drum-dried cells, etc.), diluted cells, and the like.

The *Lactobacillus pentosus* TUA4337L strain in the present invention can be used in a single form or a combination of two or more kinds of forms so long as the strain has proliferation ability in the intestinal tract. Although a total

TABLE 1

| | |
|---|---|
| Bacterial Morphology | *Bacillus* |
| Gram Staining | Positive |
| Mobility | Absent |
| Spore | Absent |
| End Spore | Absent |
| Catalase Reaction | Negative |
| Growth at 15° C. | ○ |
| Growth at 40° C. | ○ |
| Aerobic Growth | ○ |
| Anaerobic Growth | ○ |
| pH at Growth | 3.0-12.5 |

TABLE 2

| Sugar Assimilation Activity | | Sugar Assimilation Activity | | Sugar Assimilation Activity | |
|---|---|---|---|---|---|
| Glycerol | + | D-Mannitol | + | D-Raffinose | + |
| Erythritol | − | D-Sorbitol | + | Starch | − |
| D-Arabinose | − | Methyl-αD-Glucopyranoside | + | Glycogen | − |
| L-Arabinose | + | N-Acetylglucosamine | + | Xylitol | − |
| D-Ribose | + | Amygdalin | + | Gentiobiose | + |
| D-Xylose | + | Arbutin | + | D-Turanose | + |
| L-Xylose | − | Ferric Citrate-Aesculin | + | D-Lixose | − |
| D-Adonitol | − | Salicin | + | D-Tagatose | − |
| Methyl-βD-xylopyranoside | − | D-Cellobiose | + | D-Fucose | − |
| D-Galactose | + | D-Maltose | + | L-Fucose | − |
| D-Glucose | + | D-Lactose | + | D-Arabitol | − |
| D-Fructose | + | D-Melibiose | + | L-Arabitol | − |
| D-Mannose | + | D-Sucrose | + | Gluconate | + |
| L-Sorbose | − | D-Trehalose | + | 2-Ketogluconate | − |
| Dulcitol | − | Inulin | − | 5-Ketogluconate | − |
| Inositol | − | D-Melezitose | − | | | content in the composition of the present invention is not particularly limited, the total content is usually from 0.00001 to 99.9% (g/g), and especially preferably from 0.0001% to 50% (g/g) or so. Alternatively, the number of bacterial cells is preferably within the range of from $1.0 \times 10^2$ to $1.0 \times 10^{12}$ cells/g, and more preferably within the range of from $1.0 \times 10^6$ to $1.0 \times 10^{12}$ cells/g. The above "cells/g" can be expressed in viable bacteria as "CFU/g." The lactic acid bacteria of the present invention may be used in combination with a strain having an action other than the action of proliferating in the intestinal tract.

The composition of the present invention can contain carriers, basal agents, and/or additives and the like which are ordinarily used in the food field, pharmaceutical formulation fields and the like within the range that would not impair the effects of the present invention, so long as the composition contains a *Lactobacillus pentosus* TUA4337L strain having proliferation ability in the intestinal tract. Concretely, the composition includes various ingredients such as known sweeteners, acidifiers, and vitamins, and other agents such as excipients, binders, disintegrants, lubricants, correctives, dissolution aids, suspensions, coating agents, and stabilizers.

In addition, the composition of the present invention can optionally contain one or more kinds of known components such as cosmetic ingredients, and agents for preventing or ameliorating lifestyle-related diseases, in order to add other useful actions.

The form of the composition of the present invention is not particularly limited so long as the composition is in the form in which *Lactobacillus pentosus* TUA4337L strain having proliferation ability in the intestinal tract can be ingested in the body, and the form is exemplified by beverages or food containing the strain, from the viewpoint of exhibiting the effects of the strain, tablet forms ingestible as supplements, and the like, from the viewpoint of conveniently ingesting the composition. Concrete examples include, for example, various forms such as tablets, capsules, health-care drinks, seasonings, processed foods, desserts, and confectionaries. Among these forms, those provided as fermented foods are preferred. The fermented food is a generic name of food fermented with vegetable lactic acid bacteria, and beverages are included therein. Although the kinds of the fermented food are not particularly limited, the fermented food includes, for example, fermented milks, lactic acid bacteria beverages, fermented soy-milks, those obtained by fermenting fruits and vegetables, such as pickled vegetables, kimchee, wines, soybean paste (miso), and soy sauce; fermented fruit juice yogurt in which fruit juices, vegetable juices and the like are fermented.

Here, the beverage or food in which the lactic acid bacteria of the present invention is blended, in other words, the beverage or food containing a *Lactobacillus pentosus* TUA4337L strain having proliferation ability in the intestinal tract, when ingested, exhibits a high action of blocking fat absorption, as compared to a case where lactic acid bacteria not having proliferation ability in the intestinal tract are ingested, and its action continues; therefore, it is considered that as a food with health claims or healthy food having continuous action of blocking fat absorption, it is possible to provide an indication that such beverage or food is usable in blocking weight gains or reducing weight, or usable in preventing obesity or ameliorating obesity, or further usable in dieting. The food with health claims as used herein means a food with health claims ordained by the Ministry of Health, Labour and Welfare, which includes food with nutritional functional claims and food for specified heath use, and the food with health claims or healthy food may be any one of foods and beverages.

The composition of the present invention can be prepared in accordance with a known method in the food field, the pharmaceutical formulation field and the like, depending upon the forms thereof.

The composition of the present invention is properly set and not in a certain level depending upon its form, the purposes of ingestion, and age, body weight and symptoms of the subjects intended to ingest the composition, and, for example, it is preferable that the composition is orally ingested in an amount, in terms of the amount of lactic acid bacteria, of $1.0 \times 10^6$ cells or more/kg body weight per day, in a single dose to several divided doses. In addition, the amount of the bacterial cells ingested in a day is, on a dry basis, preferably from 0.00001 to 1 g, more preferably from 0.0001 to 0.2 g, and even more preferably from 0.0003 to 0.002 g, per about 50 kg body weight of one adult. For example, since the lactic acid bacteria of the present invention have the property of blocking fat absorption, and have proliferation ability in the intestinal tract, the composition of the present invention may be ingested together with a high-fat diet, or before a high-fat diet, in an amount so that the amount of lactic acid bacteria would be within the above range. The composition may be ingested once a day at breakfast, from the viewpoint of continuously exhibiting the action of blocking fat absorption. The "ingested" as used herein means "ingestion" and/or "administration."

The subjects intended to ingest the composition as used herein are preferably human in need of action of blocking fat absorption, and may be pet animals and the like.

Thus, by ingesting the composition of the present invention, the fat absorption from the intestinal tract can be blocked. Therefore, the present invention also provides a fat absorption blocking agent comprising *Lactobacillus pentosus* having proliferation ability in the intestinal tract, for blocking absorption of a fat derived from diet from the intestinal tract.

In addition, the present invention provides a method for blocking fat absorption, characterized in that the method comprises using a composition containing the above *Lactobacillus pentosus* TUA4337L strain in an effective amount in an individual in need of blocking fat absorption.

The individual in need of blocking fat absorption is not particularly limited so long as the individual is an individual with a disease which is found to have some therapeutic effects by blocking fat absorption. The individual is exemplified by, for example, an individual having obesity, or a disease such as diabetes, hyperlipemia, hypertension, or arteriosclerosis caused by obesity. In addition, for the purpose of preventing or ameliorating the above disease, the above individual also includes an individual who is concerned about body weight, an individual who is concerned about a blood sugar level, an individual who is concerned about blood pressure, and the like.

The effective amount refers to an amount that blocks fat absorption when the TUA4337L strained is administered to the above individual, as compared to an individual without administration. The concrete effective amount is properly set and is not certain depending upon the dosage forms, the methods of administration, the purposes of use, and age, body weight, symptoms and the like of individuals. Here, the administration is intended to embrace all the embodiments of administration, ingestion, internal medication, and drinking.

EXAMPLES

The present invention will be specifically described hereinbelow by the Examples, without intending to limit the scope of the present invention to the following Examples.

Example 1

Screening Using Proliferation Ability in Artificial Intestinal Solution as Index Among the lactic acid bacteria owned by the present inventors, the proliferation ability in an artificial intestinal solution was evaluated for about 480 strains which were mainly vegetable lactic acid bacteria (including JCM strains).

Concretely, first, each of the lactic acid bacteria was inoculated from a glycerol stock to an MRS medium (Difco Laboratories) (10 mL) in an amount of 1 v/v % each, and the bacterial cells were cultured at 35° C. for 16 to 17 hours. Next, $OD_{660}$ of each culture medium (absorbance at 660 nm) was measured with a spectrophotometer UV-1600 (Shimadzu Corporation), and a 100 µL solution prepared with the MRS medium so that $OD_{660}$ of each culture medium would be 10 was inoculated to an artificial intestinal solution (10 mL) of the composition shown hereinbelow. Thereafter, the bacterial cells were cultured at 37° C. for 6 hours while gently shaking, and $OD_{660}$ was then measured to obtain a proliferation fold ($OD_{660}$ after 6 hours/$OD_{660}$ at inoculation). The representative screening results are shown in Table 3 and FIG. 1.

<Artificial Intestinal Solution (pH 6.45)>

| | |
|---|---|
| MRS Medium | 9 mL |
| 10 w/v % bile acid (Wako Pure Chemical Industries, Ltd.) solution | 1 mL |
| 1 w/v % Pancreatin (from Porcine: SIGMA) | 100 µL |

Here, the bile acid solution and the pancreatin solution, which were made sterile by treating the solution with a 0.22 µm filter (PVDF membrane, manufactured by Millipore), were used.

TABLE 3

| Genera, Species | Strain | $OD_{660}$ after 6 hours | Proliferation Fold (times) ($OD_{660}$ after 6 hours/$OD_{660}$ at Inoculation) |
|---|---|---|---|
| Lactobacillus pentosus | TUA4337L (Present Invention) | 2.93 | 29.3 |
| | JCM1558 | 0.73 | 7.3 |
| | 1 | 1.55 | 15.5 |
| | 2 | 1.79 | 17.9 |
| | 3 | 1.54 | 15.4 |
| | 4 | 1.90 | 19.0 |
| | 5 | 1.68 | 16.8 |
| | 6 | 1.93 | 19.3 |
| | 7 | 1.60 | 16.0 |
| | 8 | 1.60 | 16.0 |
| | 9 | 1.78 | 17.8 |
| | 10 | 0.78 | 7.8 |
| | 11 | 1.68 | 16.8 |
| | 12 | 1.42 | 14.2 |
| | 13 | 1.37 | 13.7 |
| | 14 | 0.96 | 9.6 |
| | 15 | 1.46 | 14.6 |
| Lactobacillus plantarum | JCM1149 | 1.53 | 15.3 |
| | 16 | 1.63 | 16.3 |
| | 17 | 1.70 | 17.0 |
| | 18 | 1.42 | 14.2 |
| | 19 | 1.59 | 15.9 |
| Lactobacillus brevis | JCM1059 | 0.68 | 6.8 |
| | 20 | 1.18 | 11.8 |
| | 21 | 0.63 | 6.3 |
| | 22 | 0.58 | 5.8 |
| | 23 | 0.61 | 6.1 |
| | 24 | 0.65 | 6.5 |
| Lactobacillus casei | JCM1134 | 0.14 | 1.4 |
| | 25 | 0.94 | 9.4 |
| | 26 | 0.10 | 1.0 |
| | 27 | 0.12 | 1.2 |
| | 28 | 0.12 | 1.2 |
| | 29 | 0.11 | 1.1 |
| | 30 | 0.13 | 1.3 |
| Lactobacillus fermentum | JCM1173 | 0.27 | 2.7 |
| | 31 | 0.45 | 4.5 |
| | 32 | 0.45 | 4.5 |
| | 33 | 0.69 | 6.9 |
| | 34 | 0.93 | 9.3 |
| Lactobacillus acidophilus | JCM1132 | 0.19 | 1.9 |
| Lactobacillus delbrueckii subsp. bulgaricus | JCM1012 | 0.06 | 0.6 |
| Lactobacillus gasseri | JCM1131 | 0.08 | 0.8 |
| Lactobacillus helveticus | JCM1120 | 0.07 | 0.7 |
| Lactobacillus rhamnosus | JCM1136 | 0.17 | 1.7 |

As a result, it can be seen that the proliferation folds are more likely to be high in *Lactobacillus pentosus* and *Lactobacillus plantarum*, among which the *Lactobacillus pentosus* TUA4337L strain has an especially high proliferation fold and excellent proliferation ability in the intestinal tract.

Example 2

Evaluation of In Vivo Proliferation Ability in Intestinal Tract

Mice subjected to a high-fat diet ad libitum were administered with the TUA4337L strain prepared as follows, and the number of bacteria excreted was quantified. Concretely, C57BL/6J mice (10-week old, male) were administered in a single dose with about $1.0 \times 10^9$ lactic acid bacteria cells (corresponding to 250 µL of bacterial cell suspension) at 10 o'clock in the morning (n=5), using the administration sample prepared as follows.

<Preparation of Administration Samples (Viable Bacteria-Containing Samples)>

[1] inoculating TUA4337L strain from a glycerol stock to an MRS medium (30 mL) in an amount of 1 v/v %;
[2] culturing bacterial cells (35° C., 20 hours);
[3] centrifuging the culture medium (8,000 rpm, 5 min) to remove the supernatant, and suspending in 30 mL of PBS (−);
[4] centrifuging the suspension of [3] (8,000 rpm, 5 min) to remove the supernatant, and re-suspending in 5 mL of PBS(−);
[5] counting the number of bacteria with a microscope; and
[6] dispensing a solution containing 20,000,000,000 cells to a 15 mL centrifugation tube, centrifuging (8,000 rpm, 5 min) the solution to remove supernatant, and thereafter suspending in 5 mL of a liquid feed (high-fat diet 60 kcal % FAT:

Research Diet) to prepare a bacterial cell suspension (liquid feed was prepared with PBS(−)).

Thereafter, all the stools of two-day portions were collected in 4 divided times (the afternoon of the day the test started, the morning and the afternoon of the following day, and the morning of the day after the following day), the number of bacteria for all the stools was quantified by the following method, and the rate of increase in TUA4337L strain in the intestine in each of mice (the number of bacteria for all the stools/the number of administered bacteria) was calculated. The results are shown in Table 4.

<Method for Measuring the Number of Bacteria According to Real-Time PCR>

[1] adding 1 mL of PBS(−) to 100 mg of stools (wet weight basis), and then disrupting the stools with a spatula;
[2] collecting a 100 mg portion of the stools to an Eppendorf tube (registered trademark), centrifuging (15,000 rpm, 5 min) the stools to remove supernatant, and suspending the precipitation in 1 mL of PBS(−) (the procedures of centrifuging to suspending being repeated twice);
[3] removing supernatant from the suspension of [2], and thereafter extracting DNA from the suspension with a kit (QIAamp DNA Stool Mini Kit: QIAGEN) (the cell disruption being carried out by repeating the procedures three times of adding 300 mg of glass beads (150 to 212 µm: SIGMA), 300 µL of phenol/chloroform/isoamyl alcohol (25:24:1), and 900 µL of buffer ASL (reagents in the kit) to the stools, centrifuging the mixture with MULTI-BEADS SHOCKER MB-200 (YASUI KIKAI) at 3,000 rpm for 1 minute, and allowing to stand on ice for 1 minute); and
[4] quantifying the lactic acid bacteria in the contents of the intestinal tract according to real-time PCR under the conditions shown hereinbelow:

((Conditions for Real-Time PCR))

(1) Ten microliters of SYBR Premix Ex Taq II (Takara Bio), 0.8 µL of each primer (10 µM), 0.4 µL of ROX reference Dye II, 6 µL of sterile water, and 2 µL of a DNA solution are mixed, to prepare a liquid reaction mixture for PCR. As primers, the following primers specifically detecting 16S rDNA of *Lactobacillus pentosus* and *Lactobacillus plantarum* are used (the 16S rDNA sequences of *Lactobacillus pentosus* and *Lactobacillus plantarum* being 100% identical).

```
primer 1:
                                (SEQ ID NO: 2)
5'-GCAAGTCGAACGAACTCTGGTATT-3' primer 2:
                                (SEQ ID NO: 3)
5'-CGGACCATGCGGTCCAA-3'
```

(2) PCR is performed with 7500 Real Time PCR System (Applied Biosystems), comprising, subsequent to a treatment at 95° C. for 30 seconds, carrying out a total of 60 cycles of reactions, wherein one cycle consists of 95° C. for 5 seconds and 60° C. for 34 seconds. The copy number per one gram of the contents of intestinal tract is obtained from the fluorescent intensity obtained, a total amount of contents of the intestinal tract, and the dilution folds.
(3) Separately, the copy number of 16S rDNA per one cell is obtained, and the copy number is converted to the number of bacteria. Here, it is confirmed in the mice not administered with the lactic acid bacteria that both *Lactobacillus pentosus* and *Lactobacillus plantarum* are not detected according to the above real-time PCR.

TABLE 4

| Individual No. | Number of Bacteria of TUA4337L in Stools (cells) | Increased Rate (Number of Bacteria per Entire Stools/Number of Bacteria Administered) |
|---|---|---|
| 1 | $3.6 \times 10^9$ | 3.6 |
| 2 | $1.9 \times 10^9$ | 1.9 |
| 3 | $2.6 \times 10^9$ | 2.6 |
| 4 | $1.6 \times 10^9$ | 1.6 |
| 5 | $1.4 \times 10^9$ | 1.4 |
| Mean | $2.2 \times 10^9$ | 2.2 |

Example 3

Effects of Blocking Weight Gains

Figure 2:
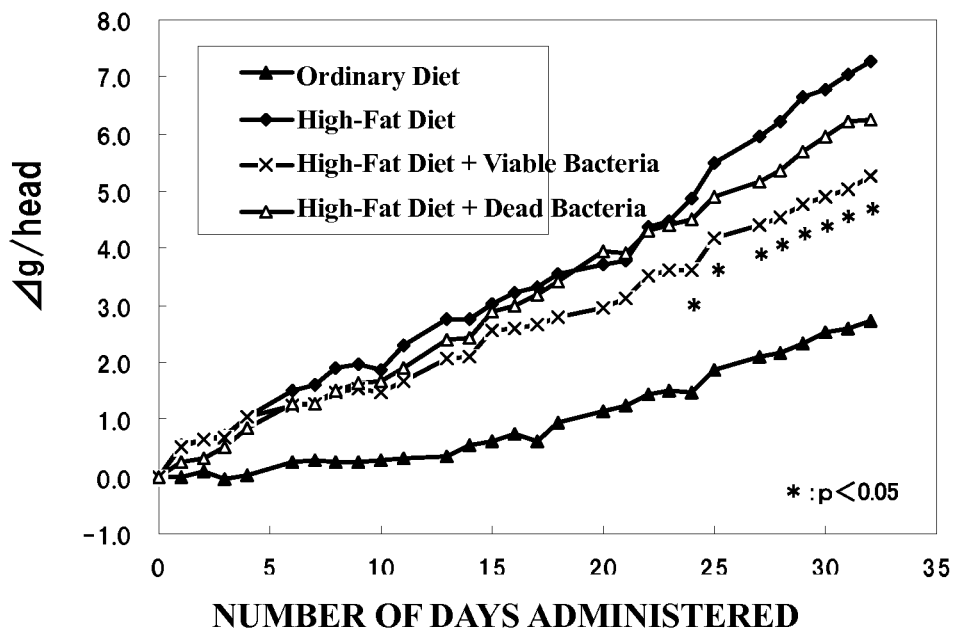
FIG. 2 is a graph showing the transition of weight gains, wherein "*" marks in the figure show that there is a significant difference ($p<0.05$) based on the high-fat diet group.

C57BL/6J mice (8-week-old, male) were grouped into four groups of an ordinary diet group, a high-fat diet group, a high fat diet+viable bacteria group, and a high-fat diet+dead bacteria group (n=10 each), and each of the groups was continuously given with the diets as shown in the following Table 5 for 32 days, and the body weights were measured daily and a mean was calculated. The transition in the mean is shown in FIG. 2. Here, intergroup comparisons were conducted using a t-test with a significant level of 0.05.

Concretely, as to diet, each group of Table 5 was given with each solid feed ad libitum. The high-fat diet+viable bacteria group was administered with an administration sample prepared in the same manner as in Example 2. The high-fat diet+dead bacteria group was administered with an administration sample prepared as follows so that the lactic acid bacteria would be contained in an amount of about 1,000,000,000 cells per day. On the other hand, the ordinary diet group was administered with 250 µL of PBS(−) not containing the lactic acid bacteria, and the high-fat diet group was administered with 250 µL of a liquid feed not containing the lactic acid bacteria.

TABLE 5

| | Diet | |
|---|---|---|
| Group | Solid Diet | Lactic Acid Bacteria Administered |
| Ordinary Diet Group | 10 kcal % FAT | — |
| High-Fat Diet Group | 60 kcal % FAT | — |
| High-Fat Diet + Viable Bacteria Group | 60 kcal % FAT | TUA4337L Viable Bacteria |
| High-Fat Diet + Dead Bacteria Group | 60 kcal % FAT | TUA4337L Dead Bacteria |

* 10 kcal % FAT (Research Diet)
60 kcal % FAT (Research Diet)

<Preparation of Administration Samples (Dead Bacteria-Containing Samples)>

[1] inoculating TUA4337L strain in an amount of 1 v/v % from a glycerol stock to an MRS medium (30 mL);
[2] culturing the bacterial cells (35° C. for 20 hours);
[3] centrifuging the culture medium (8,000 rpm, 5 min) to remove supernatant, and thereafter suspending in 30 mL of PBS(−);
[4] centrifuging the suspension of [3] (8,000 rpm, 5 min) to remove supernatant, and thereafter re-suspending in 5 mL of PBS(−);
[5] counting the number of bacteria with a microscope;
[6] dispensing a solution containing 20,000,000,000 cells to a 15 mL centrifugation tube, centrifuging the solution (8,000 rpm, 5 min) to remove supernatant, thereafter adding 5 mL of an artificial gastric fluid (125 mM NaCl, 7 mM KCl, pH 1.0) thereto, stirring the mixture, and allowing to stand for 60 minutes; and

[7] centrifuging the solution of [6] (8,000 rpm, 5 min) to remove supernatant, and thereafter suspending in 5 mL of a liquid feed (60 kcal % FAT) to prepare a bacterial cell suspension.

As a result, the group administered with the TUA4337L viable bacteria showed a significant effect of blocking weight gains, as compared to the control (the high-fat diet group). Also, the administration of viable bacteria was more effective than the administration of dead bacteria. It is considered that the *Lactobacillus pentosus* TUA4337L strain proliferated in the intestinal tract, thereby effectively influencing the host.

Example 4

Effects of Blocking Fat Absorption

Figure 3:
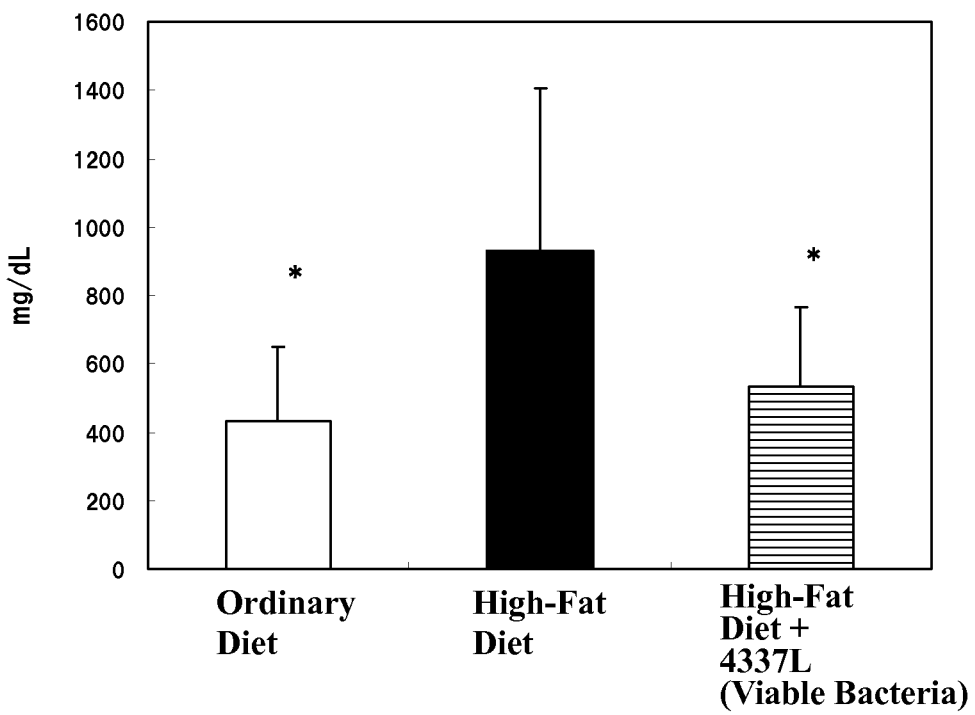
FIG. 3 is a graph showing the amount of triglyceride in sera, wherein "*" marks in the figure show that there is a significant difference ($p<0.05$) based on the high-fat diet group.

The group constituents of the ordinary diet group, the high-fat diet group, and the high-fat diet+viable bacteria group in Example 3 (n=12 each) were each continued to give the same contents of diets as in Example 3 for 2 weeks. Thereafter, the groups were fasted overnight, and administered with an olive oil (nacalai tesque) (5 mL/kg), and further dissected after 3 hours to collect sera from the vena cava. The triglyceride (TG) in sera was measured with Triglyceride E-Test Wako (Wako Pure Chemicals Industries, Ltd.). The results are shown in FIG. 3. Here, the intergroup comparisons were conducted by a significance difference judgment by a t-test with a significant level of 0.05.

As a result, the high-fat diet group was found to show the clear likeliness of increasing the TG in blood as compared to the ordinary diet group. Therefore, it is considered that if a high-fat diet is continued to be ingested, a body would more easily absorb a fat. In addition, the group administered with TUA4337L viable bacteria was found to have blocking of increase in TG in blood, as compared to the control (high-fat diet group). Therefore, one of the mechanisms of the effects of blocking weight gains is considered to be blocking of fat absorption, which was effective even after one day from the administration of the TUA4337L viable bacteria, so that it is considered to exhibit effects continuously.

Concrete formulations of the composition containing a *Lactobacillus pentosus* TUA4337L strain of the present invention are exemplified hereinbelow.

Production Example 1

Tablet

A medicament containing the TUA4337L strain (tablet) is produced in accordance with a method shown hereinbelow.

The amount 66.7 g of a dry ground product of a TUA4337L strain is mixed together with 232.0 g of lactose and 1.3 g of magnesium stearate, and the mixture is subjected to tabletting with a single-punch tabletting machine, to produce a tablet having a diameter of 10 mm and a weight of 300 mg.

Production Example 2

Yogurt

A mixture obtained by mixing milk, powdered skim milk, and water is prepared, and the mixture is sterilized with heating, cooled to 40° C. or so, and inoculated with a TUA4337L strain as a starter, and allowed to stand in a fermentation chamber to be fermented. Here, the fermentation temperature while allowing to stand can be appropriately selected. In addition, in order to control the oxygen concentration that remains dissolved at the beginning of fermentation low, the fermenting mixture may be subjected to a replacement treatment with an inert gas such as nitrogen. The TUA4337L fermented milk thus obtained is added to a commercially available milk and allowed to stand for 3 days to prepare yogurt.

Production Example 3

Lactic Acid Bacteria Beverage

Raw materials shown in Table 6 are mixed using a TUA4337L strain to prepare a lactic acid bacteria beverage.

TABLE 6

| Composition | Parts by Weight |
| --- | --- |
| TUA4337L Fermented Milk Containing 21% Milk Solid Content | 14.76 |
| Fructose-Glucose Liquid Sugar | 13.31 |
| Pectin | 0.5 |
| Citric Acid | 0.08 |
| Flavor | 0.15 |
| Water | 71.2 |
| Entire Amount | 100 |

Production Example 4

Fruit Juice Fermented Beverage and Vegetable Juice Fermented Beverage

TUA4337L is inoculated in an amount of 2% by weight to peach fruit juice, and cultured at 30° C. for 38 hours, to produce a peach fermented fruit juice. In addition, a carrot juice is fermented in the same manner to produce a carrot fermented juice.

INDUSTRIAL APPLICABILITY

Since the composition of the present invention contains lactic acid bacteria having proliferation ability in the intestinal tract, when ingested in the body, the lactic acid bacteria survive to the intestinal tract and proliferate, whereby the fat absorption can be blocked, and the weight gains can be blocked, so that the composition can be suitably used for the purposes of dieting effects.

SEQUENCE FREE TEXT

SEQ ID NO: 1 of the Sequence Listing is a nucleotide sequence of recA of *Lactobacillus pentosus* TUA4337L.

SEQ ID NO: 2 of the Sequence Listing is a nucleotide sequence of a *Lactobacillus pentosus/plantarum*-specific primer.

SEQ ID NO: 3 of the Sequence Listing is a nucleotide sequence of a *Lactobacillus pentosus/plantarum*-specific primer.

The invention claimed is:

1. A method of blocking fat absorption, comprising: administering a composition comprising a *Lactobacillus pentosus* TUA4337L strain (accession number: NITE BP-1479) to an individual in need of blocking fat absorption, in an amount effective to block fat absorption in the individual.

2. A method of ameliorating obesity, comprising: administering a composition comprising a *Lactobacillus pentosus* TUA4337L strain (accession number: NITE BP-1479) to an individual in need of amelioration of obesity, in an amount effective to ameliorate obesity.

3. A method of blocking weight gain, comprising: administering a composition comprising a *Lactobacillus pentosus* TUA4337L strain (accession number: NITE BP-1479) to an individual in need of blocking weight gain, in an amount effective to block weight gain.

* * * * *

SEQUENCE LISTING

<160> NUMBER OF SEQ ID NOS: 3

<210> SEQ ID NO 1
<211> LENGTH: 535
<212> TYPE: DNA
<213> ORGANISM: Lactobacillus pentosus 4337L
<220> FEATURE:
<223> OTHER INFORMATION: a gene encoding recA of Lactobacillus pentosus
      4337L
<220> FEATURE:
<221> NAME/KEY: n
<222> LOCATION: 423, 442
<223> OTHER INFORMATION: a or g or c or tu/, unknown or other

<400> SEQUENCE: 1
gcgattatgc ggatgggtga cgctgcccag acgaccattt caacaatttc cagcgggtca      60
ctagccttag atgacgcatt aggcgttggt ggttacccac gtggccgaat cgttgaaatt     120
tatggccctg aaagttccgg taaaacgacc gttgcactac acgcggtcgc tgaagttcaa     180
aagcaaggcg ggacggccgc ctatatcgat gctgaaaacg ccttggatcc ggtttacgcg     240
gaacatttag gtgtcaacat tgatgatttg ttactttcac aaccagatac tggtgaacaa     300
ggtcttgaaa tcgcggatgc tttagtttcc agtggcgcgg ttgatatctt agttgtcgat     360
tcagttgcgg cgttagtacc acgggccgaa attgaaggtg aaatgggtga cgcccacgtt     420
ggnttacaag cccggttaat gncacaagcg ttgcggaagt tatccgggac tttgaacaag     480
acaaagacca tcgcactatt tattaaccaa attcgtgaaa aagttggcgt gatgt          535

<210> SEQ ID NO 2
<211> LENGTH: 24
<212> TYPE: DNA
<213> ORGANISM: Artificial Sequence
<220> FEATURE:
<223> OTHER INFORMATION: primer for the Lactobacillus pentosus

<400> SEQUENCE: 2
gcaagtcgaa cgaactctgg tatt                                             24

<210> SEQ ID NO 3
<211> LENGTH: 17
<212> TYPE: DNA
<213> ORGANISM: Artificial Sequence
<220> FEATURE:
<223> OTHER INFORMATION: primer for the Lactobacillus pentosus

<400> SEQUENCE: 3
cggaccatgc ggtccaa                                                     17